United States Patent
Chen (10) Patent No.: US 6,764,465 B2
(45) Date of Patent: Jul. 20, 2004

(54) SYRINGE WITH RETRACTABLE NEEDLE AND SAFETY LOCK

(76) Inventor: Long Hsiung Chen, 2F, No. 2-1, Lane 22, Szu Wei Road, Taipei (TW)

(*) Notice: Subject to any disclaimer, the term of this patent is extended or adjusted under 35 U.S.C. 154(b) by 0 days.

(21) Appl. No.: 10/176,669

(22) Filed: Jun. 24, 2002

(65) Prior Publication Data

US 2003/0236504 A1 Dec. 25, 2003

(51) Int. Cl.[7] .............................................. A61M 5/00
(52) U.S. Cl. ...................... 604/110; 604/111; 604/195; 604/201; 604/240; 604/244; 600/577
(58) Field of Search ............................... 604/110, 111, 604/187, 195, 201, 198, 200, 240, 244; 600/576, 577

(56) References Cited

U.S. PATENT DOCUMENTS

| | | | | |
|---|---|---|---|---|
| 4,425,120 A | * | 1/1984 | Sampson et al. | 604/198 |
| 4,643,199 A | * | 2/1987 | Jennings et al. | 600/576 |
| 4,699,614 A | * | 10/1987 | Glazier | 604/110 |
| 4,801,295 A | * | 1/1989 | Spencer | 604/198 |
| 4,832,694 A | * | 5/1989 | Raphael et al. | 604/110 |
| 4,844,089 A | * | 7/1989 | Roberti | 600/577 |
| 4,883,466 A | * | 11/1989 | Glazier | 604/110 |
| 4,892,107 A | * | 1/1990 | Haber | 600/576 |
| 5,067,490 A | * | 11/1991 | Haber | 600/578 |
| 5,070,885 A | * | 12/1991 | Bonaldo | 600/576 |
| 5,217,436 A | * | 6/1993 | Farkas | 604/187 |
| 5,222,945 A | * | 6/1993 | Basnight | 604/110 |
| 5,263,942 A | * | 11/1993 | Smedley et al. | 604/195 |
| 5,405,326 A | * | 4/1995 | Haber et al. | 604/110 |
| 5,445,620 A | * | 8/1995 | Haber et al. | 604/232 |
| 5,891,105 A | * | 4/1999 | Mahurkar | 604/195 |
| 6,093,170 A | * | 7/2000 | Hsu et al. | 604/110 |
| 6,102,894 A | * | 8/2000 | Dysarz | 604/110 |
| 6,117,112 A | * | 9/2000 | Mahurkar | 604/194 |
| 6,152,901 A | * | 11/2000 | Arruego et al. | 604/195 |
| 6,206,856 B1 | * | 3/2001 | Mahurkar | 604/195 |
| 6,511,440 B2 | * | 1/2003 | Chen | 600/576 |

* cited by examiner

Primary Examiner—Brian L. Casler
Assistant Examiner—Jeremy Thissell
(74) Attorney, Agent, or Firm—Rosenberg, Klein & Lee (57) ABSTRACT

The invention provides a safety syringe for extracting blood, with retractable or removable needle that can be retracted into the syringe body or removed after use and safety locks that lock the retractable needle in an extended position during use and in a retracted position after use to ensure that the syringe is not reused or that the needle is not inadvertently extended. When retracted, the needle assembly is cocked at an angle identifying the syringe as used and adding further protection to prevent the needle from being inadvertently extended and exposed from the tube. These safety features work in conjunction to enhance the usability and increase the safety of the syringe. Thereby protecting medical workers from being injured by an exposed needle or contaminated by disease or infection from contact with the patient's blood present on a used needle.

13 Claims, 7 Drawing Sheets

SYRINGE WITH RETRACTABLE NEEDLE AND SAFETY LOCK

BACKGROUND OF THE INVENTION

1. Field of the Invention

The present invention relates to a medical syringe. More specifically, the present invention discloses a safety syringe with a retractable needle and safety lock, for extracting blood.

2. Description of the Prior Art

Syringes are utilized by medical workers for a variety of uses including injecting and withdrawing blood samples.

However, due to the fixed nature of conventional syringes, accidents are far to common. Such accidents include, puncture by exposed needles and contamination or infection caused by contact with residual blood left on the needle or syringe after use. Due to the harmful or fatal nature of such diseases, contaminates, or infections, such accidents endanger the lives of medical personal working in doctor's offices, clinics or hospitals.

Medical personal can be further exposed to danger if syringes are not disposed of properly after use. Additionally, if a syringe is re-used, accidentally or other wise, a patient may be infected or contaminated by contact with residual blood left on the used syringe.

Therefore, there is a need for an improved safety syringe for extracting blood, with retractable needle that can be retracted into the syringe body after use, having safety locks that lock the retractable needle in an extended position during use and in a retracted position after use to ensure that the syringe is not reused or that the needle is not inadvertently extended so as to provide more safety for medical workers and patients. Additionally, the needle assembly can be removed from the syringe after use and properly disposed and the syringe plastic material may be recycled accordingly.

SUMMARY OF THE INVENTION

To achieve these and other advantages and in order to overcome the disadvantages of the conventional method in accordance with the purpose of the invention as embodied and broadly described herein, the present invention provides an improved safety syringe for extracting blood, with retractable needle that can be retracted into the syringe body after use and safety locks that lock the retractable needle in an extended position during use and in a retracted position after use to ensure that the syringe is not reused or that the needle is not inadvertently extended so as to provide more safety for medical workers.

The safety syringe basically comprises a tube with guiding track, a needle retaining base, a needle mounting base, and a button. The button comprises a button face, a prong, an end tip, and a ridge.

The needle mounting base comprises a mount whereby a needle can be attached to the needle mounting base. A ridge formed on the needle mounting base to mate with a matching groove in the needle retaining base. A bump provides a snapping lock for holding the needle mounting base onto the needle retaining base. Note, the ridge and groove may be inverted to provide a groove in the needle mounting base and a ridge in the needle retaining base. A flow tube extends through the needle mounting base with one end exposed in an opening of the mount in a top side of the needle mounting base and another end exposed in the bottom of the needle mounting base. The end of the flow tube has a sharp tip for puncturing the seal of the vacuum vial. The flow tube allows for blood to flow from the needle into the vacuum vial. The end of the flow tube may or may not extend to be exposed through the top of the opening and is positioned to allow mating with the needle. A top tab protrudes from the top end of the needle mounting base. A bottom tab protrudes from the bottom end of the needle mounting base. The top tab and bottom tab provide a slot for mating with the end tip of the button thereby affixing the button and the needle mounting base.

The needle retaining base comprises an opening with a groove for mating with the needle retaining base and the ridge. This arrangement allows the needle retaining base to affix in a correct position to the needle mounting base. A slot in the top of the needle retaining base comprises a groove to mate with a mating ridge on the button. This arrangement allows the button to be affixed to the needle retaining base and still provide free in and out movement of the button. A notch is provided to increase flexibility in the sidewall of the needle retaining base. A slot is provided in the sidewall of the needle retaining base to mate with a mating ridge on the inside of the tube. This allows the needle retaining base to be locked in position during use of the safety syringe.

The tube comprises a cap that can be opened to allow for a vacuum vial to be inserted into the tube or closed before or after use to prevent contact with the flow tube. The cap has tabs that allow the cap to be snapped and held onto slots provided in flanges of the tube. A tab is provided for snapping into a mating notch in the wall of the tube after the cap is opened. A slide track is provided in the side of the tube. The slide track comprises a slanted safety lock slot, a zigzag notch, an L section, and an ear tab. The slide track guides the button attached to the needle retaining base in the correct position as the needle retaining base travels through the tube. A locking ridge on the inside of the tube mates with the slot in the sidewall of the needle retaining base to allow the needle retaining base to be locked in position during use of the safety syringe. An opening in the top and side of the tube comprises a closed section and an open section. The closed section prevents the needle mounting base from being inadvertently removed. The open section allows the needle mounting base to be removed if desired when the button is moved into the L section of the tube. The ear tab functions to lock the button, the needle retaining base, and the needle mounting base in a fixed place. The needle mounting base may be removed from the safety syringe by pushing in the button when the button is locked in the L section by the ear tab.

To prepare the safety syringe for use, a vacuum vial with seal is inserted into the opening of the tube until the tip of the flow tube punctures the seal of the vacuum vial. When the seal is punctured, the vacuum pressure in the vial will act as a suction and draw blood from the patient, through the needle and the flow tube, and into the vial. The slot is provided in the sidewall of the needle retaining base to mate with a mating ridge on the inside of the tube. This allows the needle retaining base to be locked in position during use of the safety syringe.

The needle, needle mounting base, needle retaining base, and button can be placed in an in-use or ready to use position. As mentioned previously, the slot is provided in the sidewall of the needle retaining base to mate with a mating ridge on the inside of the tube. This allows the needle retaining base to be locked in position during use of the safety syringe and prevents the needle assembly from inadvertently retracting into the tube. Note, the zigzag notch in the slide track is provided for safety protection to prevent the needle assembly from inadvertently extending or protruding from the tube or from moving into an in-use position. The saw tooth nature of the zigzag notch will catch or inhibit movement of the button. In a closed or retracted position, the button is snapped into the slanted safety lock slot of the slide track. Due to the slanted nature of the safety lock slot, the needle assembly is cocked into an angled position. This prevents the needle from inadvertently protruding from the end of the tube and endangering the safety of medical workers. This also easily identifies the safety syringe as used and prevents re-use of the safety syringe.

A top tab protrudes from the top end of the needle mounting base. A bottom tab protrudes from the bottom end of the needle mounting base. The top tab and bottom tab provide a slot for mating with the end tip of the button thereby affixing the button and the needle mounting base. Note, in this position the closed section of the tube holds the needle mounting base in place and prevents the needle mounting base from being inadvertently removed. An opening in the top and side of the tube comprises a closed section and an open section. As mentioned previously, the closed section prevents the needle mounting base from being inadvertently removed. The open section allows the needle mounting base to be removed if desired when the button is moved into the L section of the tube. The ear tab functions to lock the button, the needle retaining base, and the needle mounting base in a fixed place. The needle mounting base may be removed from the safety syringe by pushing in the button when the button is locked in the L section by the ear tab. In this way, the needle mounting base and needle can be easily removed from the tube. Thereafter, the needle mounting base and needle can be disposed of properly. Since the materials of the button, tube, and needle retaining base are of similar materials, these components can be recycled after the needle and needle mounting base have been removed.

These and other objectives of the present invention will become obvious to those of ordinary skill in the art after reading the following detailed description of preferred embodiments.

It is to be understood that both the foregoing general description and the following detailed description are exemplary, and are intended to provide further explanation of the invention as claimed.

BRIEF DESCRITPION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE PREFERRED EMBODIMENTS

Reference will now be made in detail to the preferred embodiments of the present invention, examples of which are illustrated in the accompanying drawings. Wherever possible, the same reference numbers are used in the drawings and the description to refer to the same or like parts.

Figure 1:
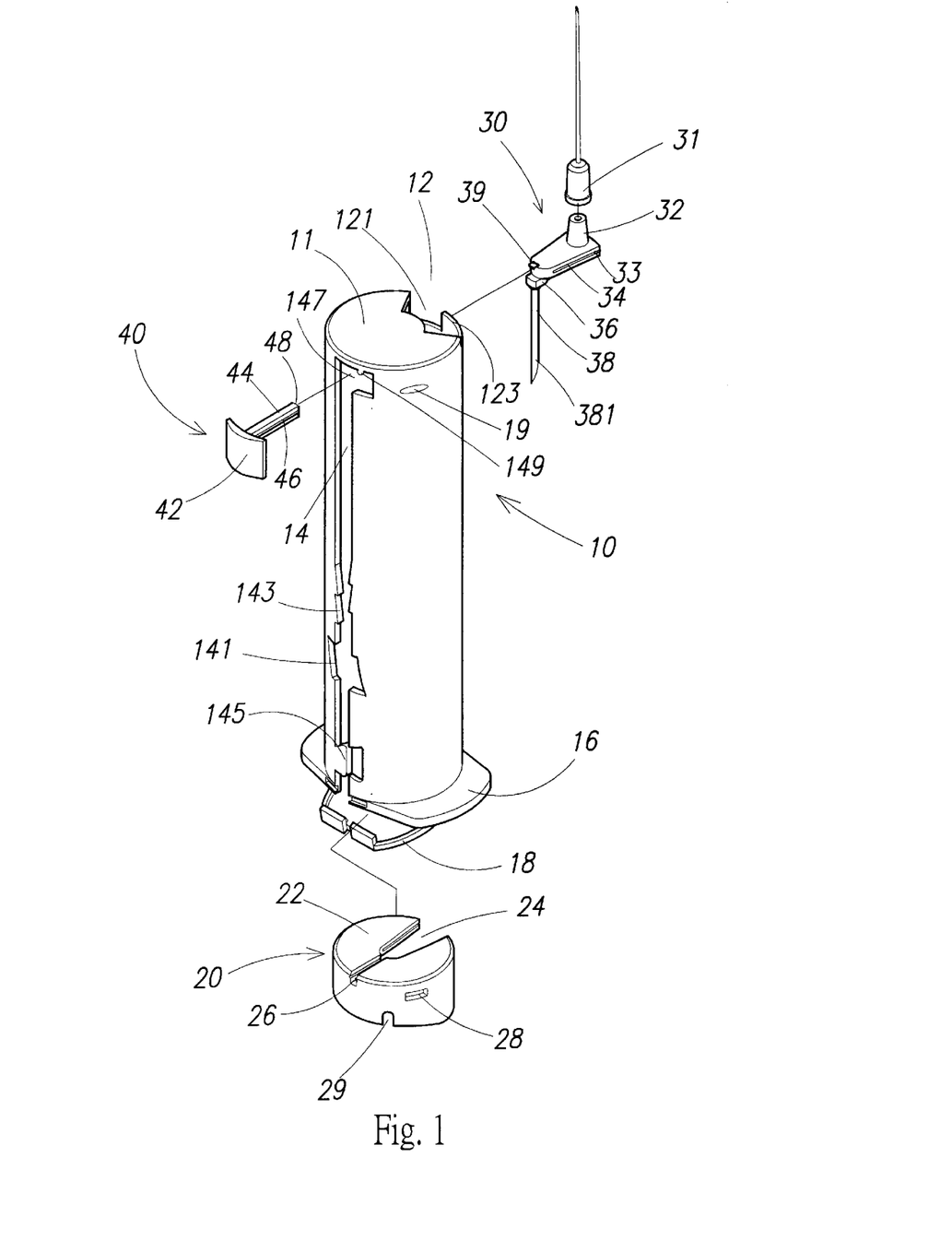
FIG. 1 is a drawing illustrating a safety syringe with retractable needle and safety locks according to an embodiment of the present invention.
Figure 2:
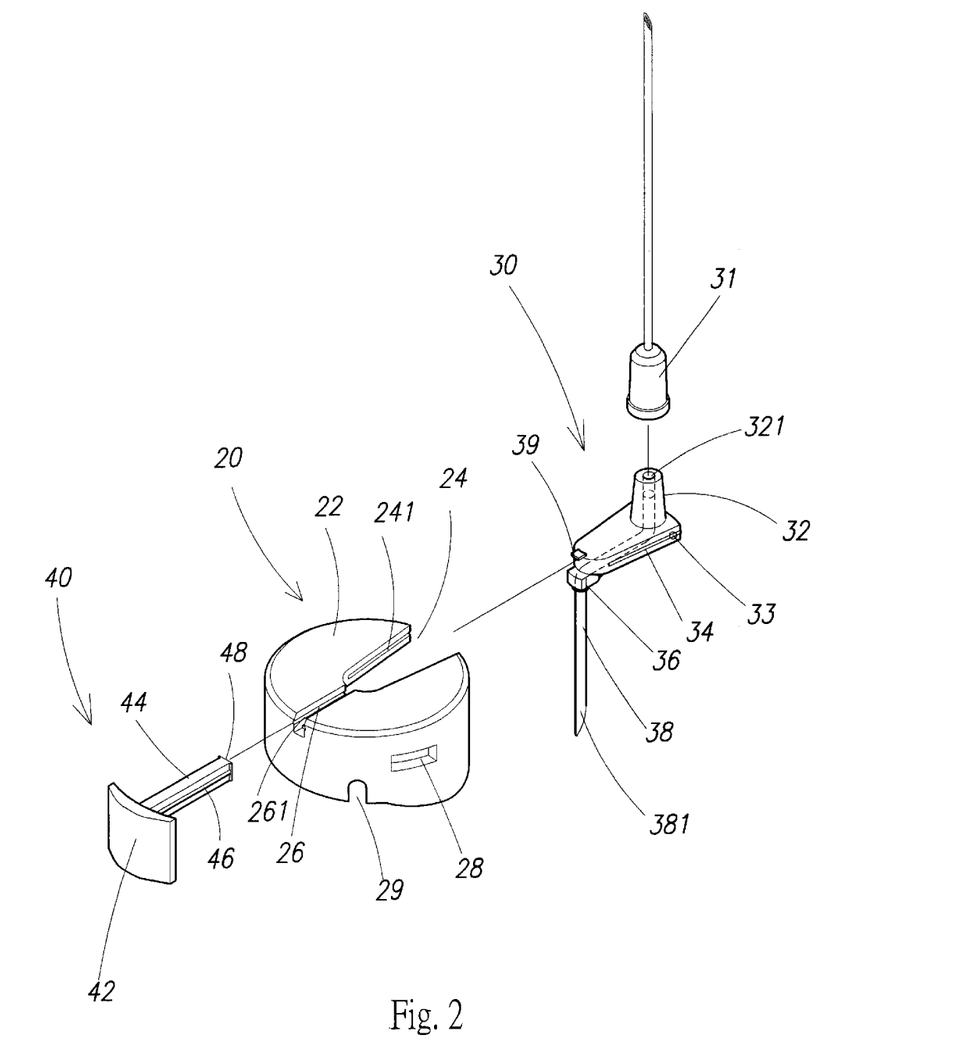
FIG. 2 is a drawing illustrating a needle and needle retaining base according to an embodiment of the present invention.

Refer to FIG. 1, which is a drawing illustrating a safety syringe with retractable needle and safety locks according to an embodiment of the present invention and to FIG. 2, which is a drawing illustrating a needle and needle mounting base according to an embodiment of the present invention.

The safety syringe basically comprises a tube 10 with guiding track, a needle retaining base 20, a needle mounting base 30, and a button 40.

The button 40 comprises a button face 42, a prong 44, an end tip 48, and a ridge 46.

The needle mounting base 30 comprises a mount 32 whereby a needle 31 can be attached to the needle mounting base 30. A ridge 34 formed on the needle mounting base 30 to mate with a matching groove 241 in the needle retaining base 20. A bump 33 provides a snapping lock for holding the needle mounting base 30 onto the needle retaining base 20. Note, the ridge 34 and groove 24 may be inverted to provide a groove in the needle mounting base 30 and a ridge in the needle retaining base 20.

A flow tube 38 extends through the needle mounting base 30 with one end exposed in an opening 321 of the mount 32 in a top side of the needle mounting base 30 and another end 381 exposed in the bottom of the needle mounting base 30. The end 381 of the flow tube 38 has a sharp tip for puncturing the seal of the vacuum vial (not shown). The flow tube 38 allows for blood to flow from the needle 31 into the vacuum vial. The end of the flow tube 38 may or may not extend to be exposed through the top of the opening 321 and is positioned to allow mating with the needle 31.

A top tab 39 protrudes from the top end of the needle mounting base 30. A bottom tab 36 protrudes from the bottom end of the needle mounting base 30. The top tab 39 and bottom tab 36 provide a slot for mating with the end tip 48 of the button 40 thereby affixing the button 40 and the needle mounting base 30.

The needle retaining base 20 comprises an opening 24 with a groove 241 for mating with the needle retaining base 20 and the ridge 34. This arrangement allows the needle retaining base 20 to affix in a correct position to the needle mounting base 30.

A slot 26 in the top 22 of the needle retaining base 20 comprises a groove 261 to mate with a mating ridge 46 on the button 40. This arrangement allows the button 40 to be affixed to the needle retaining base 20 and still provide free in and out movement of the button 40.

A notch 29 is provided to increase flexibility in the sidewall of the needle retaining base 20.

A slot 28 is provided in the sidewall of the needle retaining base 20 to mate with a mating ridge 19 on the inside of the tube 10. This allows the needle retaining base 20 to be locked in position during use of the safety syringe.

The tube 10 comprises a cap 18 that can be opened to allow for a vacuum vial (not shown) to be inserted into the tube 10 or closed before or after use to prevent contact with the flow tube 381. The cap 18 has tabs that allow the cap 18 to be snapped and held onto slots provided in flanges 16 of the tube 10.

A tab 145 is provided for snapping into a mating notch in the wall of the tube 10 after the cap 18 is opened.

A slide track 14 is provided in the side of the tube 10. The slide track 14 comprises a slanted safety lock slot 141, a zigzag notch 143, an L section 147, and an ear tab 149. The slide track 14 guides the button 40 attached to the needle retaining base 20 in the correct position as the needle retaining base 20 travels through the tube 10.

A locking ridge 19 on the inside of the tube mates with the slot 28 in the sidewall of the needle retaining base 20 to allow the needle retaining base 20 to be locked in position during use of the safety syringe.

An opening 12 in the top 11 and side of the tube 10 comprises a closed section 123 and an open section 121. The closed section 123 prevents the needle mounting base 30 from being inadvertently removed. The open section 121 allows the needle mounting base 30 to be removed if desired when the button 40 is moved into the L section 147 of the tube 10. The ear tab 149 functions to lock the button 10, the needle retaining base 20, and the needle mounting base 30 in a fixed place. This is particularly useful during use of the safety syringe. The needle mounting base 30 may be removed from the safety syringe by pushing in the button 40 when the button is locked in the L section 147 by the ear tab 149.

Figure 3:
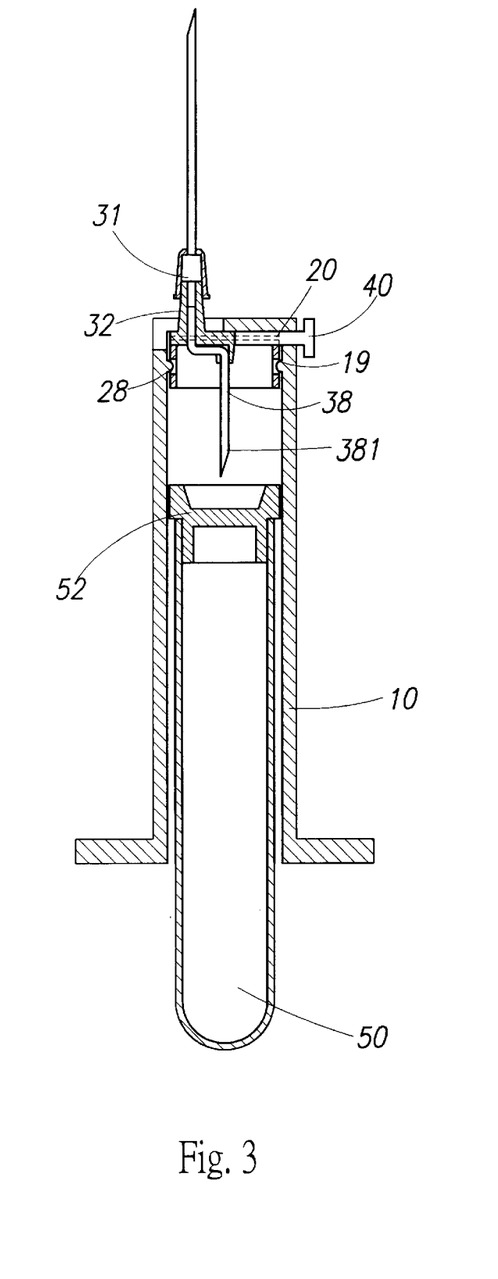
FIG. 3 is a cross section drawing illustrating a safety syringe and vacuum vial according to an embodiment of the present invention.
Figure 4:
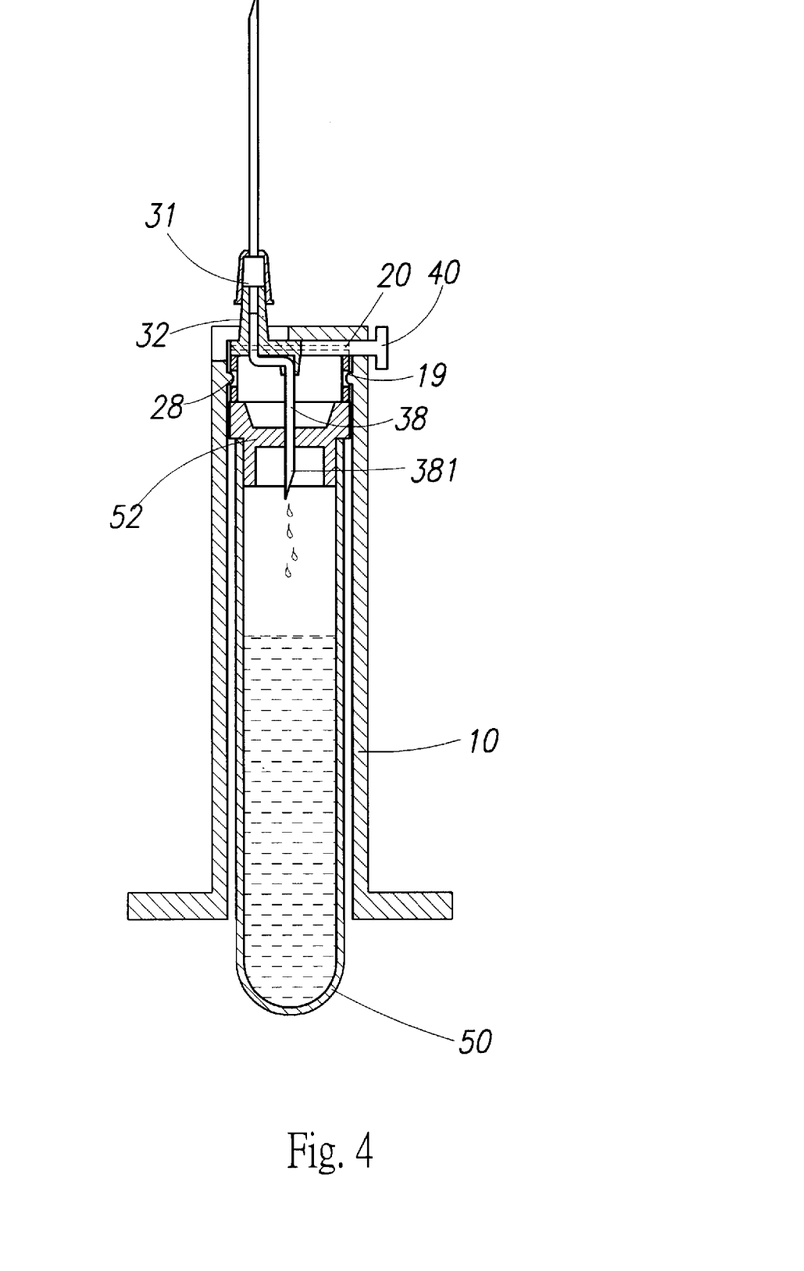
FIG. 4 is a cross section drawing illustrating a safety syringe and vacuum vial according to an embodiment of the present invention.

Refer to FIG. 3, which is a cross section drawing illustrating a safety syringe and vacuum vial according to an embodiment of the present invention and FIG. 4, which is a cross section drawing illustrating a safety syringe and vacuum vial according to an embodiment of the present invention.

To prepare the safety syringe for use, a vacuum vial 50 with seal 52 is inserted into the opening of the tube 10 until the tip 381 of the flow tube 38 punctures the seal 52 of the vacuum vial 50. When the seal 52 is punctured, the vacuum pressure in the vial 50 will act as a suction and draw blood from the patient, through the needle 31 and the flow tube 38, and into the vial 50.

Note, FIGS. 3 and 4 show in more detail a function of the slot 28 and mating ridge 19. The slot 28 is provided in the sidewall of the needle retaining base 20 to mate with a mating ridge 19 on the inside of the tube 10. This allows the needle retaining base 20 to be locked in position during use of the safety syringe.

Figure 5A:
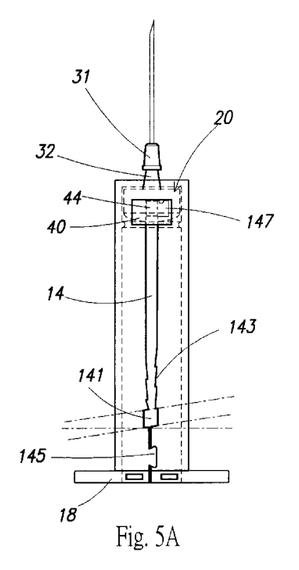
FIG. 5a is a cross section drawing illustrating a safety syringe with retractable needle and safety locks according to an embodiment of the present invention.
Figure 5B:
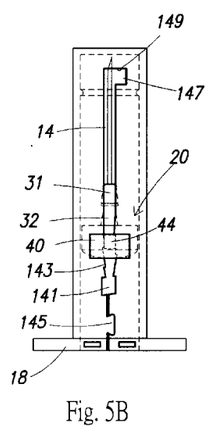
FIG. 5b is a cross section drawing illustrating a safety syringe with retractable needle and safety locks according to an embodiment of the present invention.
Figure 5C:
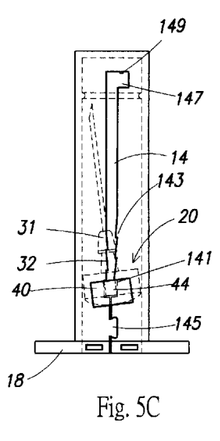
FIG. 5c is a cross section drawing illustrating a safety syringe with retractable needle in a retracted position and safety locks according to an embodiment of the present invention.

Refer to FIGS. 5a, 5b and 5c, which are cross section drawings illustrating a safety syringe with retractable needle and safety locks according to an embodiment of the present invention.

In FIG. 5a, the needle 31, needle mounting base 30, needle retaining base 20, and button are in an in-use or ready to use position. As mentioned previously, the slot 28 is provided in the sidewall of the needle retaining base 20 to mate with a mating ridge 19 on the inside of the tube 10. This allows the needle retaining base 20 to be locked in position during use of the safety syringe and prevents the needle assembly from inadvertently retracting into the tube.

In FIG. 5b, the needle 31, needle mounting base 30, needle retaining base 20, and button are in a retracting position. Note, the zigzag notch 143 in the slide track 14 is provided for safety protection to prevent the needle assembly from inadvertently extending or protruding from the tube or from moving into an in-use position. The saw tooth nature of the zigzag notch 143 will catch or inhibit movement of the button.

In FIG. 5c, the needle assembly is in a closed or retracted position. In this position, the button is snapped into the slanted safety lock slot 141 of the slide track 14. Due to the slanted nature of the safety lock slot 141, the needle assembly is cocked into an angled position. This prevents the needle 31 from inadvertently protruding from the end of the tube and endangering the safety of medical workers. This also easily identifies the safety syringe as used and prevents re-use of the safety syringe. Additionally, the slanted safety lock slot 141 prevents the end of the flow tube from protruding through the bottom of the tube body.

Figure 6A:
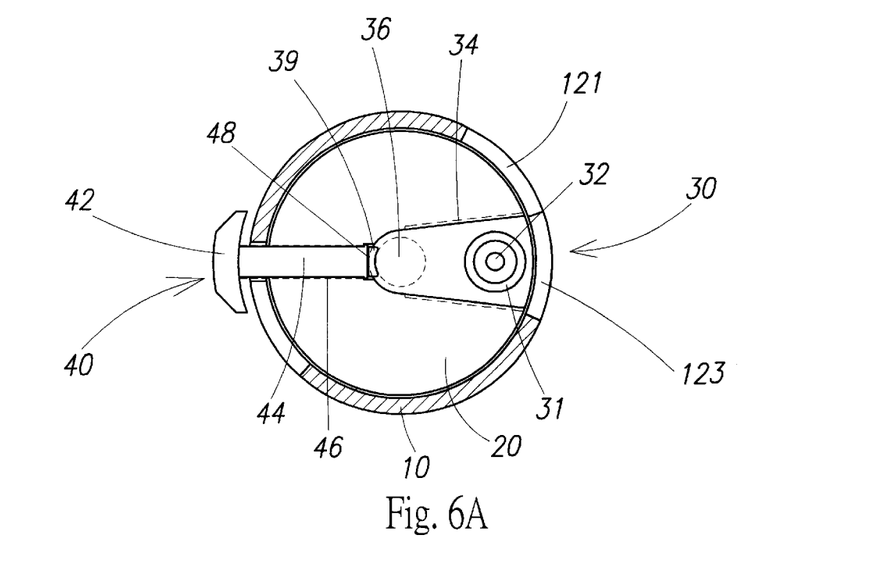
FIG. 6a is a drawing illustrating a needle retaining base and button according, to an embodiment of the present invention.
Figure 6B:
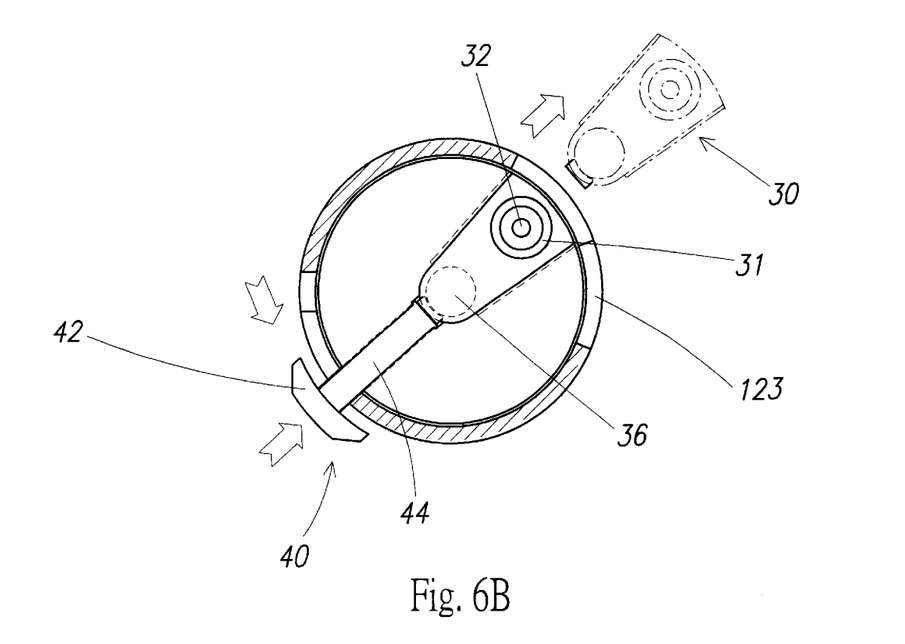
FIG. 6b is a drawing illustrating a needle retaining base and button according to an embodiment of the present invention.
Figure 7:
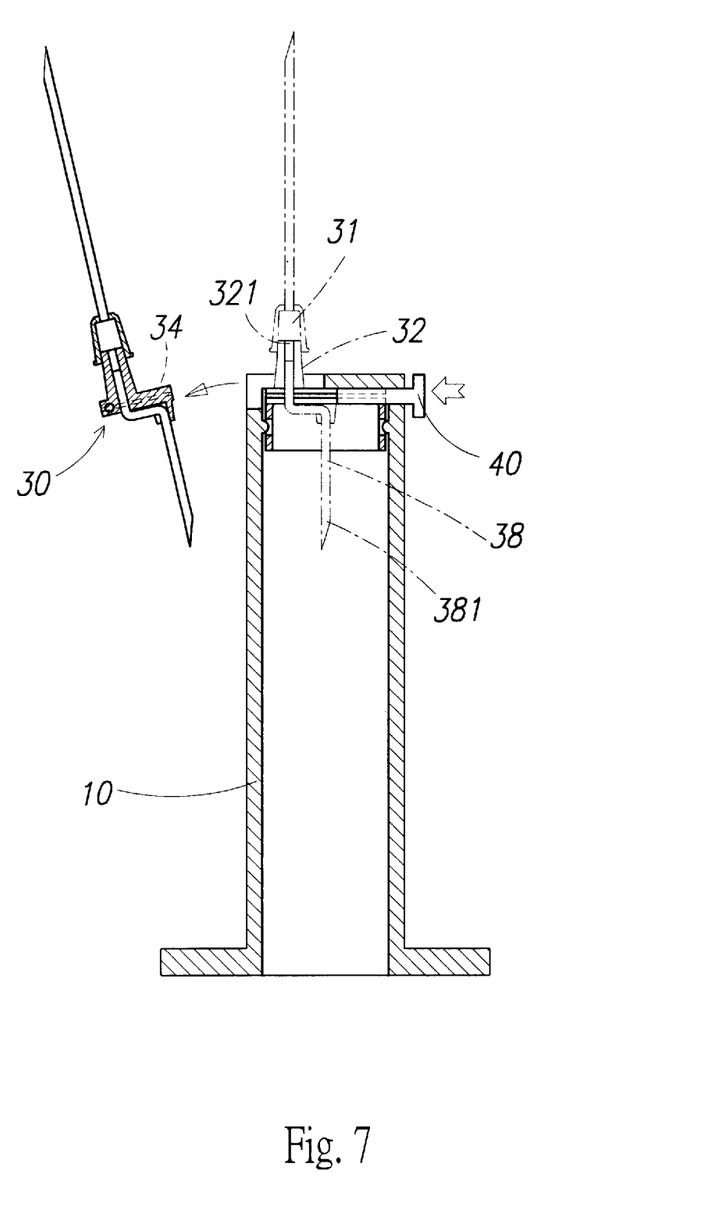
FIG. 7 is a drawing illustrating a safety syringe with removable needle according to an embodiment of the present invention.

Refer to FIGS. 6a, 6b, and 7, which are drawings illustrating a needle mounting base and button according to an embodiment of the present invention.

FIGS. 6a and 6b show detailed views of the attachable and removable nature of the button 40 and the needle mounting base 30.

In FIG. 6a, a top tab 39 protrudes from the top end of the needle mounting base 30. A bottom tab 36 protrudes from the bottom end of the needle mounting base 30. The top tab 39 and bottom tab 36 provide a slot for mating with the end tip 48 of the button 40 thereby affixing the button 40 and the needle mounting base 30. Note, in this position the closed section of the tube 10 holds the needle mounting base 30 in place and prevents the needle mounting base 30 from being inadvertently removed.

In FIGS. 6b and 7, an opening 12 in the top 11 and side of the tube 10 comprises a closed section 123 and an open section 121. As mentioned previously, the closed section 123 prevents the needle mounting base 30 from being inadvertently removed. The open section 121 allows the needle mounting base 30 to be removed if desired when the button 40 is moved into the L section 147 of the tube 10. The ear tab 149 functions to lock the button 10, the needle retaining base 20, and the needle mounting base 30 in a fixed place. The needle mounting base 30 may be removed from the safety syringe by pushing in the button 40 when the button is locked in the L section 147 by the ear tab 149.

In this way, the needle mounting base 30 and needle 31 can be easily removed from the tube 10. Thereafter, the needle mounting base 30 and needle 31 can be disposed of properly. Since the materials of the button 40, tube 10, and needle retaining base 20 are of similar materials, these components can be recycled after the needle 31 and needle mounting base 30 have been removed.

It will be apparent to those skilled in the art that various modifications and variations can be made to the present invention without departing from the scope or spirit of the invention. In view of the foregoing, it is intended that the present invention cover modifications and variations of this invention provided they fall within the scope of the invention and its equivalent.

What is claimed is:

1. A safety syringe comprising:
   a needle mounting base for providing means for attaching a needle to the safety syringe, comprising a flow tube extending through the needle mounting base and a needle mount on which a needle can be attached to the needle mounting base;
   whereby the flow tube provides a directed path for blood to flow from the needle into a vacuum vial;
   a needle retaining base for holding the needle mounting base and a button;
   the button removably attached to the needle retaining base and the needle mounting base for moving the needle mounting base and needle retaining base through a tube body; and
   the tube body with slotted track for correctly positioning the needle retaining base, the needle mounting base, and the button within the tube body;
   whereby the slotted track of the tube body comprises a slanted polygon slot for locking the button in a retracted position; and
   whereby pressing the button allows the needle mounting base to be removed from the safety syringe.

2. The safety syringe of claim 1, whereby when the button is locked in the retracted position, the needle mounting base and needle retaining base are held at an angle so as to prevent the needle from being extended or exposed from the tube body.

3. The safety syringe of claim 2, whereby when the button is locked in the retracted position, the angled bases identify the syringe as used.

4. The safety syringe of claim 1, whereby the slotted track of the tube body comprises a zigzag section to prevent the needle from being inadvertently exposed from the tube body.

5. The safety syringe of claim 1, whereby the slotted track of the tube body comprises an L section and locking tab;
   whereby a bottom of the L section provides a fully extended position stop; and
   whereby the locking tab locks the button in the fully extended position.

6. A safety syringe comprising;
   a needle mounting base for providing means for attaching a needle to the safety syringe, comprising a flow tube extending through the needle mounting base and a needle mount on which a needle can be attached to the needle mounting base;
   a needle retaining base for holding the needle mounting base and a button;
   the button removably attached to the needle retaining base and the needle mounting base for moving the needle mounting base and needle retaining base through a body tube; and
   a tube body with slotted track for correctly positioning the needle retaining base, the needle mounting base, and the button within the tube body;
   whereby the slotted track comprises a slanted polygon slot for locking the button in a retracted position; and
   whereby, when the button is locked in the retracted position, the needle mounting base and needle retaining base are held at an angle so as to prevent the needle from being extended or exposed from the tube body and identify the syringe as used.

7. The safety syringe of claim 6, whereby the slotted track of the tube body comprises a zigzag section to prevent the needle from being inadvertently exposed from the tube body.

8. The safety syringe of claim 6, whereby the slotted track of the tube body comprises an L section and locking tab;
   whereby a bottom of the L section provides a fully extended position stop; and whereby when the button is moved through the L section and past the locking tab, the locking tab locks the button in the fully extended position.

9. A safety syringe comprising:
   a needle mounting base for providing means for attaching a needle to the safety syringe, comprising a flow tube extending through the needle mounting base and a needle mount on which a needle can be attached to the needle mounting base;
   whereby the flow tube provides a directed path for blood to flow from the needle into a vacuum vial;
   a needle retaining base for holding the needle mounting base and a button;
   the button removably attached to the needle retaining base and the needle mounting base for moving the needle mounting base and needle retaining base through a tube body; and
   the tube body with slotted track for correctly positioning the needle retaining base, the needle mounting base, and the button within the tube body;
   whereby the slotted track of the tube body comprises a slanted polygon slot for locking the button in a retracted position;
   whereby pressing the button allows the needle mounting base to be removed from the safety syringe;
   whereby the tube body comprises an opening in a top and side of the tube body; and
   whereby the opening comprises a closed section for preventing the needle mounting base from being removed from the safety syringe and an open section for allowing the needle mounting base to be removed from the safety syringe.

10. The safety syringe of claim 9, whereby when the button is locked in the retracted position, the needle mounting base and needle retaining base are held at an angle so as to prevent the needle from being extended or exposed from the tube body.

11. The safety syringe of claim 10, whereby when the button is locked in the retracted position, the angled bases identify the syringe as used.

12. The safety syringe of claim 9, whereby the slotted track of the tube body comprises a zigzag section to prevent the needle from being inadvertently exposed from the tube body.

13. The safety syringe of claim 9, whereby the slotted track of the tube body comprises an L section and locking tab;
    whereby a bottom of the L section provides a fully extended position stop; and
    whereby the locking tab locks the button in the fully extended position.

* * * * *